United States Patent

Pigg

[11] Patent Number: 5,600,702
[45] Date of Patent: Feb. 4, 1997

[54] POSITIONER FOR A CHILD BEING X-RAYED

[76] Inventor: Jimmy C. Pigg, P.O. Box 772, Waynesboro, Tenn. 38485

[21] Appl. No.: 547,978

[22] Filed: Oct. 25, 1995

[51] Int. Cl.$^6$ ................................................. G03B 42/02
[52] U.S. Cl. ........................ 378/180; 378/178; 378/208
[58] Field of Search .................................... 378/177, 178, 378/179, 180, 208

[56] References Cited

U.S. PATENT DOCUMENTS

| 2,571,011 | 10/1951 | Chapman | 378/178 |
|---|---|---|---|
| 2,790,083 | 4/1957 | Snawder et al. | 378/178 |
| 2,926,256 | 2/1960 | Rankin | 378/174 |
| 3,051,832 | 8/1962 | Pigg | 378/179 |

Primary Examiner—David P. Porta
Assistant Examiner—David Vernon Bruce
Attorney, Agent, or Firm—Waddey & Patterson; Arles A. Taylor, Jr.

[57] ABSTRACT

Improvements for a positioner for a child being X-rayed are disclosed. The improvements include an improved latch for securing the carriage that supports the X-ray film cassette in a positioner for a child being X-rayed at a position after the carriage is adjusted upwards or downwards; and, the addition of resilient pads for increasing the friction between glide strips and foot members of a positioner for a child being X-rayed so that the foot members will be more effectively secured to the glide strips. The improvements also include an improved latching mechanism used in securing the film holder of the positioner for a child being X-rayed in a position as it is moved towards or away from the upstanding members that secure the child. The buttons that are used to secure the foot members to the glide strip have also been improved by providing them with a tapered bottom surface. The taper compensates for variable thickness in the foot member. An improved seat latch mechanism in a positioner for a child being X-rayed is also described. Several parts of the positioner have been improved by molding them into one piece integral units. Examples of such molded parts include the foot members that connect the side members that contain the child to the turntable; the indicia marker unit that displays X-ray impervious indicia for exposure onto the film so that various views can be identified on the X-ray film; and the seat latch of this invention.

9 Claims, 12 Drawing Sheets

POSITIONER FOR A CHILD BEING X-RAYED

BACKGROUND OF THE INVENTION

The present invention relates generally to a positioner for a child being X-rayed and more particularly to improvements in a positioner on a child being X-rayed.

A positioner for a child being X-rayed is described in U.S. Pat. No. 3,051,832 issued to Jalmer Pigg, Sr. on Aug. 28, 1962, the contents of which are incorporated herein by reference. While the device described in this patent is effective in positioning a child being X-rayed, several problems have developed with this device.

Figure 2:
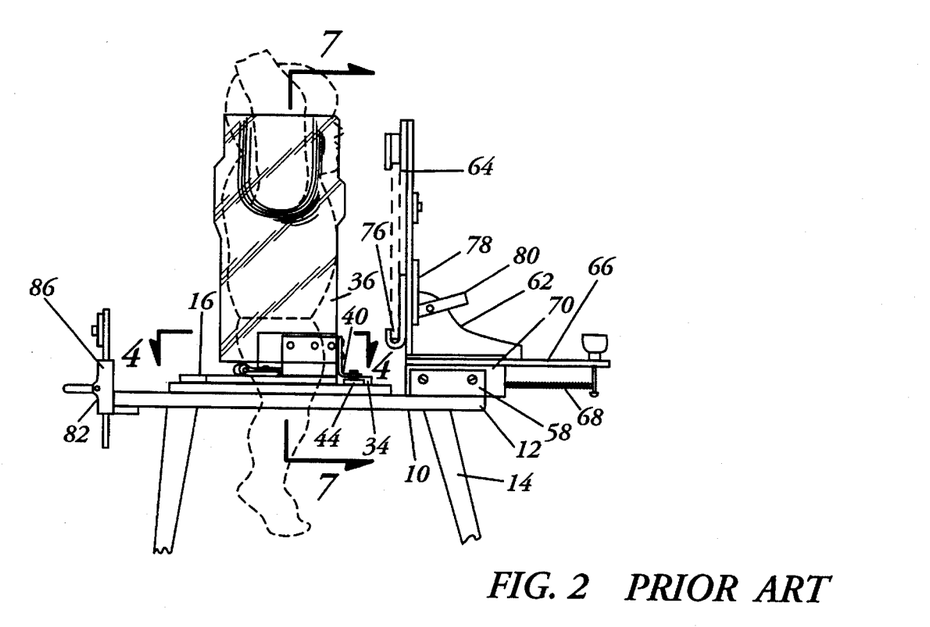
FIG. 2 is a side elevational view of the positioner of the prior art, the dotted line indicating the body of a small child or infant supported in the positioner.
Figure 3:
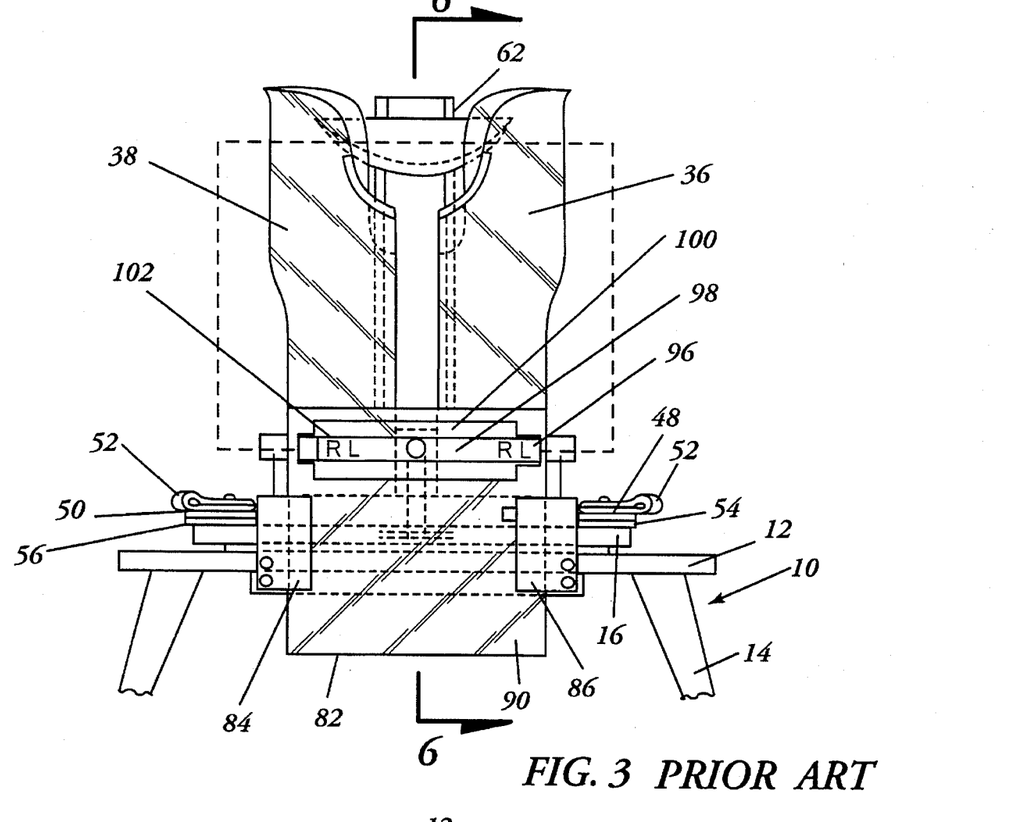
FIG. 3 is a front elevational view of the positioner of the prior art.

As best seen in FIG. 2, film holder 62 includes hooks 74 and 76 and X-ray cassette fits between these hooks. Carriage 78 supports the X-ray film cassette. Carriage 78 carries lower hook 76. Latch 80 in U.S. Pat. No. 3,051,832 patent is employed to secure carriage 78 at a position after carriage 78 is adjusted upward or downward by an X-ray technician. The problem that has developed with latch 80 is that in tightening the latch 80, the hard surface of the latch 80 is tightened against the hard surface of the film holder 62. The interaction of the two hard surfaces results in ineffective latching. The problem of ineffective latching results in over-tightening of the latch 80, which causes breakage in the film holder 62.

Figure 1:
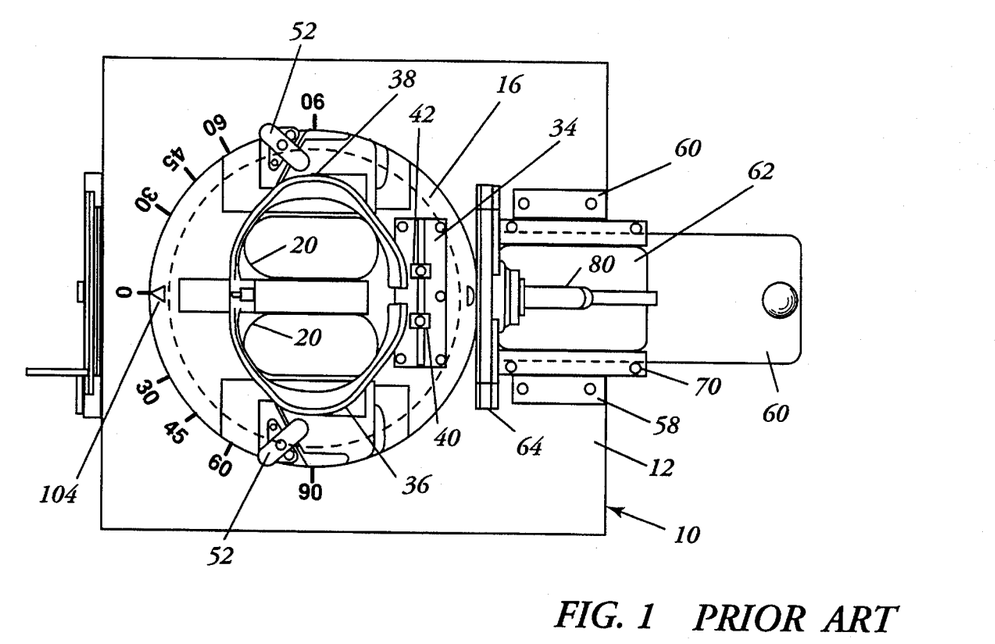
FIG. 1 is a top view of the positioner according to the prior art.
Figure 4:
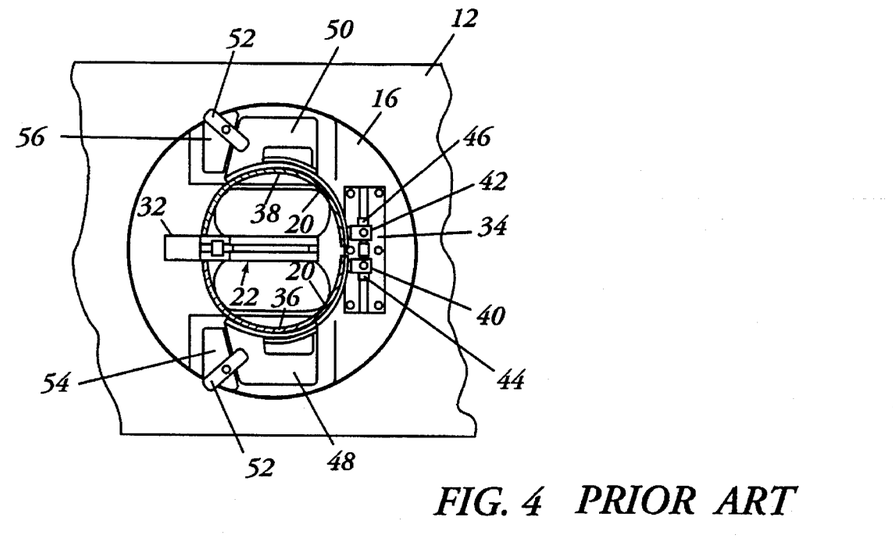
FIG. 4 is a view taken on the line 4—4 of FIG. 2, showing the side members of the positioner of the prior art in closed position.
Figure 5:
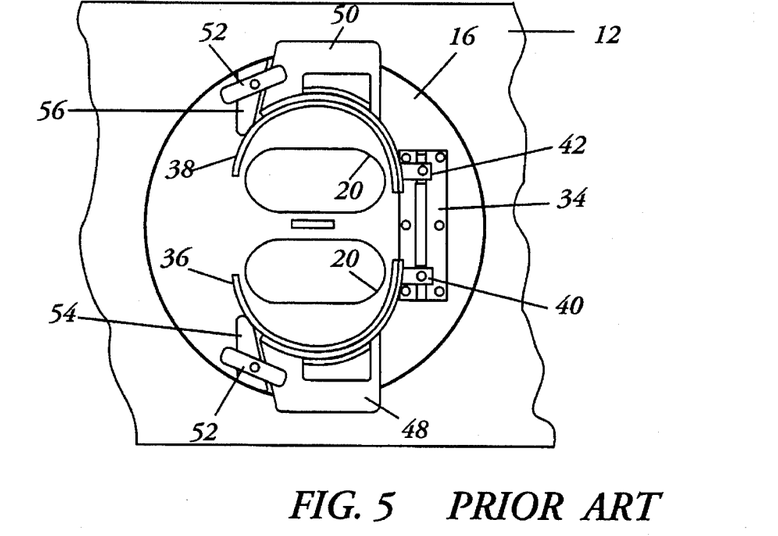
FIG. 5 is a view similar to FIG. 4, showing the side members of the positioner of the prior art in open position.

Another problem with the positioner of U.S. Pat. No. 3,051,832 occurs in the mounting area between the turn table 16 and foot members 48 and 50. Glide strips (not shown in U.S. Pat. No. 3,051,832) have been provided between turn table 16 and foot members 48 and 50. Referring to FIGS. 1, 4 and 5, when foot members 48 and 50 are secured to glide strips by means of button 52 which is rotatable to affect a wedging action on the respective foot member, the hard slick surface of the foot member cannot be secured effectively to the hard slick surface of the glide strip. This results in the connection slipping, and in some cases, the releasing of the child.

Figure 8:
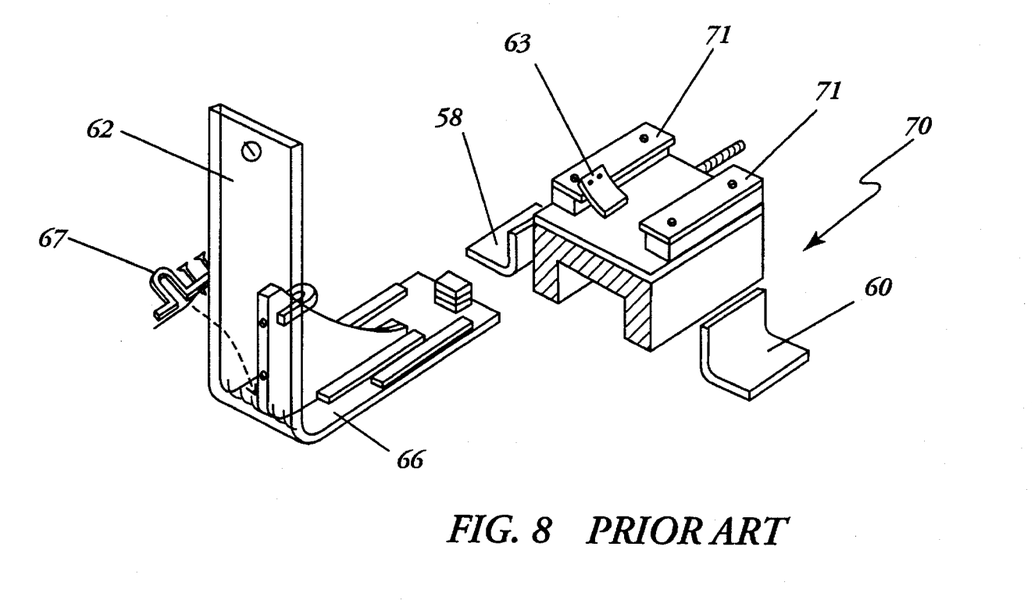
FIG. 8 is an exploded perspective view of the film holder and film holder track of prior art positioner.

A further problem with the positioner of U.S. Pat. No. 3,051,832 has developed in the latching mechanism that secures film holder 62 as it is moved towards or away from the upright members 36 and 38 that secure the child. Since the prior latching mechanism is not explicitly shown in U.S. Pat. No. 3,051,832, FIG. 8 is provided to clarify it. Referring to FIG. 8, the prior latching mechanism for film holder 62 includes a stop 63 mounted on the upright members 71 of the block 70 into which slide 66 fits, and a bent metal clip 67 mounted on slide 66, the stop 63 interacting with the bent metal clip 67 to hold the film holder 62 in place. The problem that occurs is that the metal clip 67 bends further and loses the ability to hold the film holder 62 in place.

Referring again to FIGS. 1, 4 and 5, a further problem that has developed with the positioner for a child being X-rayed as is described in U.S. Pat. No. 3,051,832 is that foot members 48 and 50 can vary in thickness. The problem is compounded by the fact that blocks 54 and 56 that support the buttons 52 that are used to secure each foot member 48 and 50 to turn table 16 are cut with a flat top surface. Since blocks 54 and 56 have a flat top surface, there is no way to increase the tightness of the interaction between buttons 52 and foot numbers 48 and 50 as buttons 52 are turned over foot members 48 and 50. Thus, buttons 52 can be ineffective in tightening down on the foot members 48 and 50 because of the variable thickness in foot members 48 and 50.

A further problem in the positioner of U.S. Pat. No. 3,051,832 has developed in sliding elements 44 and 46, which can be best seen in FIGS. 2 and 4. Each sliding element is composed of two parts and two screws and/or pins. These parts often separate, which make sliding elements 44 and 46 unusable. Sliding elements 44 and 46 vary greatly in thickness, making it difficult to manufacture and supply replacement parts for sliding elements 44 and 46.

A further problem with the positioner described in U.S. Pat. No. 3,051,832 has developed with the device for exposing identifying indicia to the X-ray film 82. The indicia on device 82 are comprised of an x-ray impervious material and are hand-glued to a piece of plexiglass. These letters constantly break loose or break off completely. The loss of the indicia prevent the technician from being able to label the X-ray as from the left or right of the patient or as an inhale or exhale view.

Figure 6:
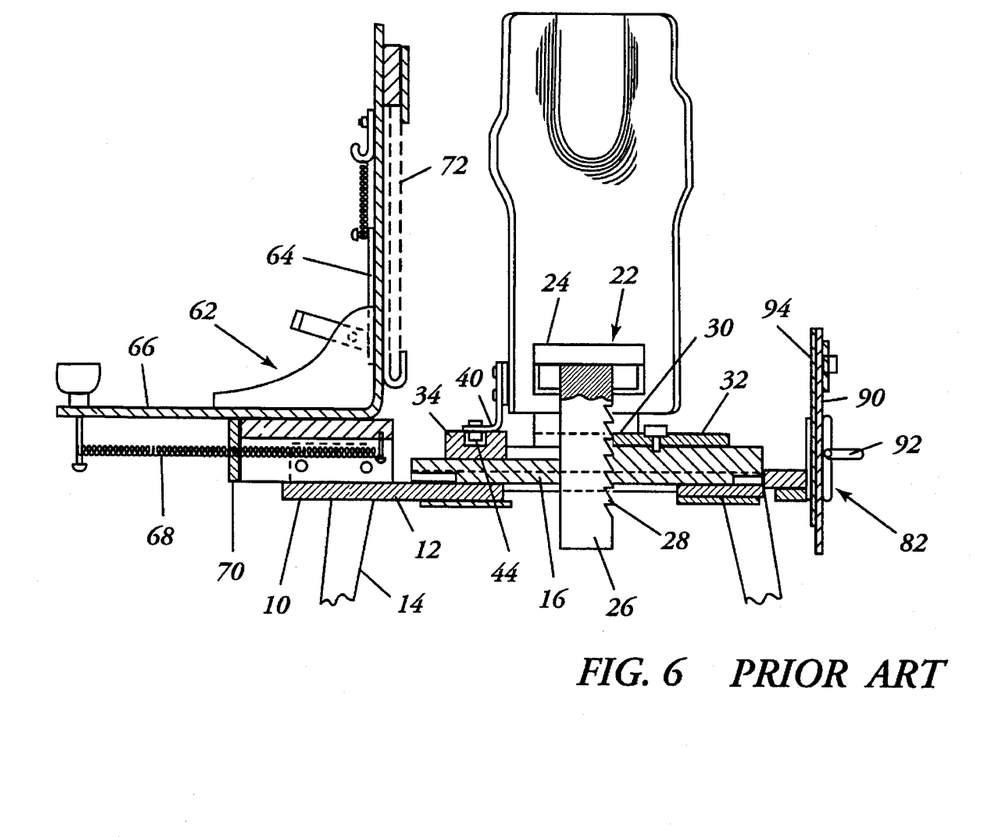
FIG. 6 is a view taken on the line 6—6 of FIG. 3.
Figure 7:
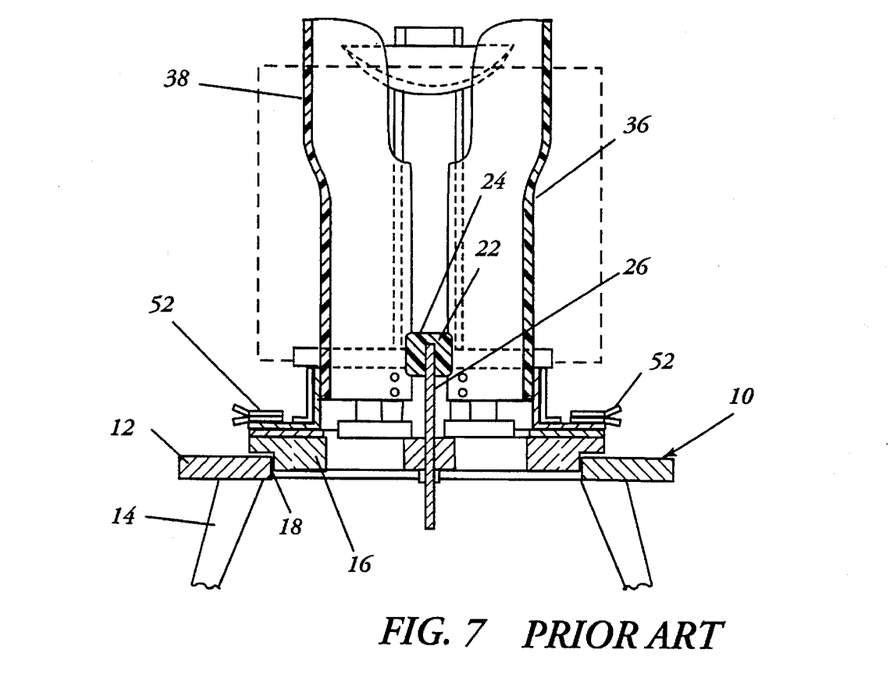
FIG. 7 is a view taken on the line 7—7 of FIG. 2.
Figure 9:
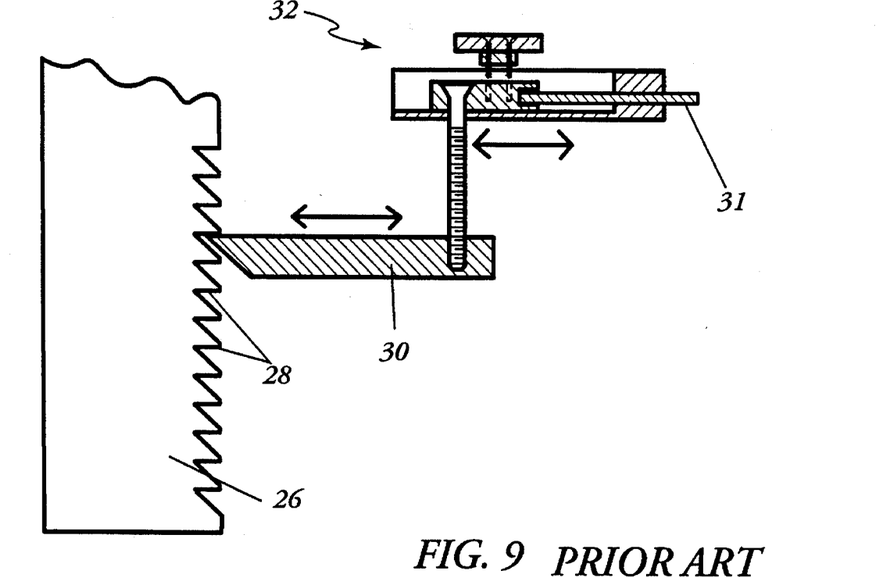
FIG. 9 is an exploded side view of the seat latch of the prior art positioner.

Another problem with the positioner of U.S. Pat. No. 3,051,832 has developed in the latching mechanism for horse member 22. As seen in FIGS. 6 and 7, horse member 22 comprises the seat of the positioner and includes a padded head 24 and a bar 26. A dog 30 is slidably mounted in a holder 32 on the upper face of the turn table 16 for movement into and out of engagement with a selected one of the pawl teeth 28 that are along one side edge of bar 26. The original seat latch consists of some nine parts that are hand cut and fitted from east acrylic sheets. These parts vary in thickness greatly. Additionally, as seen in FIG. 9, a metal pin 31 that facilitates movement of dog 30 into and out of engagement with a selected one of the pawl teeth 28, often bends and locks up the seat latch. Moreover, the variable thickness in the parts of the seat latch made the parts difficult to fit together. This results in constant binding. This combination of problems made the seat latch difficult to operate.

What is needed, then, are improvements in the positioner described in U.S. Pat. No. 3,051,832 that address these problems. Such improvements are lacking in the prior art.

SUMMARY OF THE INVENTION

It is an object of this invention to provide an improved latch for securing the carriage that supports the X-ray film cassette in a positioner for a child being X-rayed at a position after the carriage is adjusted upwards or downwards.

It is a further object of this invention to provide a means for increasing the friction between the glide strips and foot members of a positioner for a child being X-rayed so that the foot members will be more effectively secured to the glide strips.

It is yet another object of this invention to provide an improved securing means for securing the film holder of the positioner for a child being X-rayed in a position as it is moved towards or away from the upstanding members that secure the child.

It is still another object of the invention to provide improved securing means for securing the foot members of the positioner for a child being X-rayed to the turn table.

It is a further object of this invention to provide sliding elements for a positioner for a child being X-rayed that are cast as a one-piece part and where the tolerance is held to a standardized limit in the casting process.

It is yet another object of this invention to provide a device for exposing an identifying indicia to the X-ray film in a positioner for a child being X-rayed wherein the indicia are integrated with indicia supporting members so that the indicia do not break away from the indicia supporting member.

It is another object of this invention to provide an improved seat latch mechanism in a positioner for a child being X-rayed.

Improvements in a positioner for a child being X-rayed are described herein. The positioner comprises a platform having an opening therethrough, a turn table mounted in the opening in said platform for rotary movement in clockwise and counterclockwise directions, there being a pair of side-by-side spaced openings in said turn table between the perimeter thereof for the projection of the legs of a child therethrough, a horse member arranged between and spaced from each of said openings for supporting a child in a straddled position and connected to said turn table for upward and downward movement, a pair of arcuate shaped upstanding side members each transparent to light waves and X-rays arranged in face-to-face spaced relation positioned on said turn table between the perimeter and said turn table openings and connected to said turn table for limited movement toward and away from each other, and an upstanding film holder positioned on said platform adjacent to and facing said side members and supported on said platform, the film holder including latching means for latching an X-ray film cassette in place after movement of the X-ray film cassette vertically to place the X-ray film cassette between an X-ray machine and the child being X-rayed, the latching means having an end that contacts the X-ray film cassette and an end opposite the end that contacts the X-ray film cassette. One of the improvements comprises means for increasing friction mounted at the end of the latching means that contacts the X-ray film cassette and the end of the latching means opposite the end that contacts the X-ray film cassette having a greater weight than the end that contacts the X-ray film cassette.

The positioner can further comprise foot members attached to said arcuate shaped upstanding side members, glide strips mounted between said foot members and said turn table, and latching means for latching said foot members to said glide strips mounted on said glide strips. Another improvement comprises means for increasing friction mounted between said glide strips and said foot members.

The positioner can further comprise means for displaying indicia mounted on the platform such that said means for displaying indicia fall in a path of an X-ray from an X-ray machine and the X-ray film cassette, the means for displaying indicia including indicia and indicia supporting means for supporting indicia. Another improvement comprises said indicia being molded into said indicia supporting means so that said indicia are an integral unit with said indicia supporting means.

The positioner can further comprise a track into which the film holder is mounted, the film holder including a slide that fits into said track. Another improvement comprises securing means for securing the film holder when the film holder is moved towards or away from said pair of arcuate shaped upstanding members, said securing means comprising a latching means mounted on said track and stop means mounted on said slide of said film holder such that said stop means interacts with said latching means. Preferably, the stop means comprises a spring loaded pin.

The positioner can further comprise securing means for securing said foot members to said glide strips, said securing means having a mounting end and a wedging end, said securing means turnably mounted to said glide strips. The improvement comprising tightening means for tightening said securing means against said foot members. The securing means can be mounted at its said mounting end on a support means for supporting said securing means, said support means mounted to said glide strip; and wherein said tightening means comprises said support means being tapered along a top surface of said support means, said top surface lying adjacent to said securing means, such that said support means is thicker at a point where said mounting end of said securing means contacts said top surface when said wedging end of said securing means is moved over said foot members.

The positioner can further comprise a latching means for latching said horse member to said turntable, said horse member further comprising a seat member and a bar extending downward from said seat member, the bar having a plurality of receiving means for receiving said latching means along a vertical edge of said bar; the latching means comprising a base mounted to said turntable, said base having a medial slot therein and a lower surface facing said turntable, said surface having a horizontal section spaced away from said turntable and three vertical sections between said horizontal section and said turntable, two of said vertical sections being substantially parallel to one another and the third of said vertical sections connecting said parallel vertical sections and being substantially perpendicular thereto, said horizontal section and said vertical sections defining a space between said turntable and said base; a bar slidably mounted within said space, a button mounted within said base at said medial slot, said button mounted to said bar; a rod extending downward from said bar; a dog having two ends, said dog attached at one of its ends to said rod, said dog having at is other end interacting means for interacting with said receiving means of said bar of said horse member to latch said horse member in place. The improvement comprises a spring mounted within said space between said bar and said connecting vertical section of said lower surface of said base. The base can of the latching means can be cast as a one-piece part.

The positioner can comprise sliding elements mounted to a base of said arcuate shaped upstanding members, said sliding elements slidably mounted to said turntable. The improvement comprises said sliding elements being cast as a one-piece part.

DESCRIPTION OF THE PREFERRED EMBODIMENT

Reference numerals that include a prime (') refer to new and improved parts that replace the similarly numbered parts of the prior art U.S. Pat. No. 3,051,832 or to parts with no counterpart in U.S. Pat. No. 3,051,832. Reference numerals that do not include a prime (') refer to the prior art parts of the positioner as they are substantially described in U.S. Pat. No. 3,051,832. Those descriptions are herein incorporated by reference. FIGS. 1–9 describe the prior art positioner, and all reference numbers in FIGS. 1–9 correspond to reference numbers used in the descriptions of U.S. Pat. No. 3,051,832, herein incorporated by reference.

Figure 12:
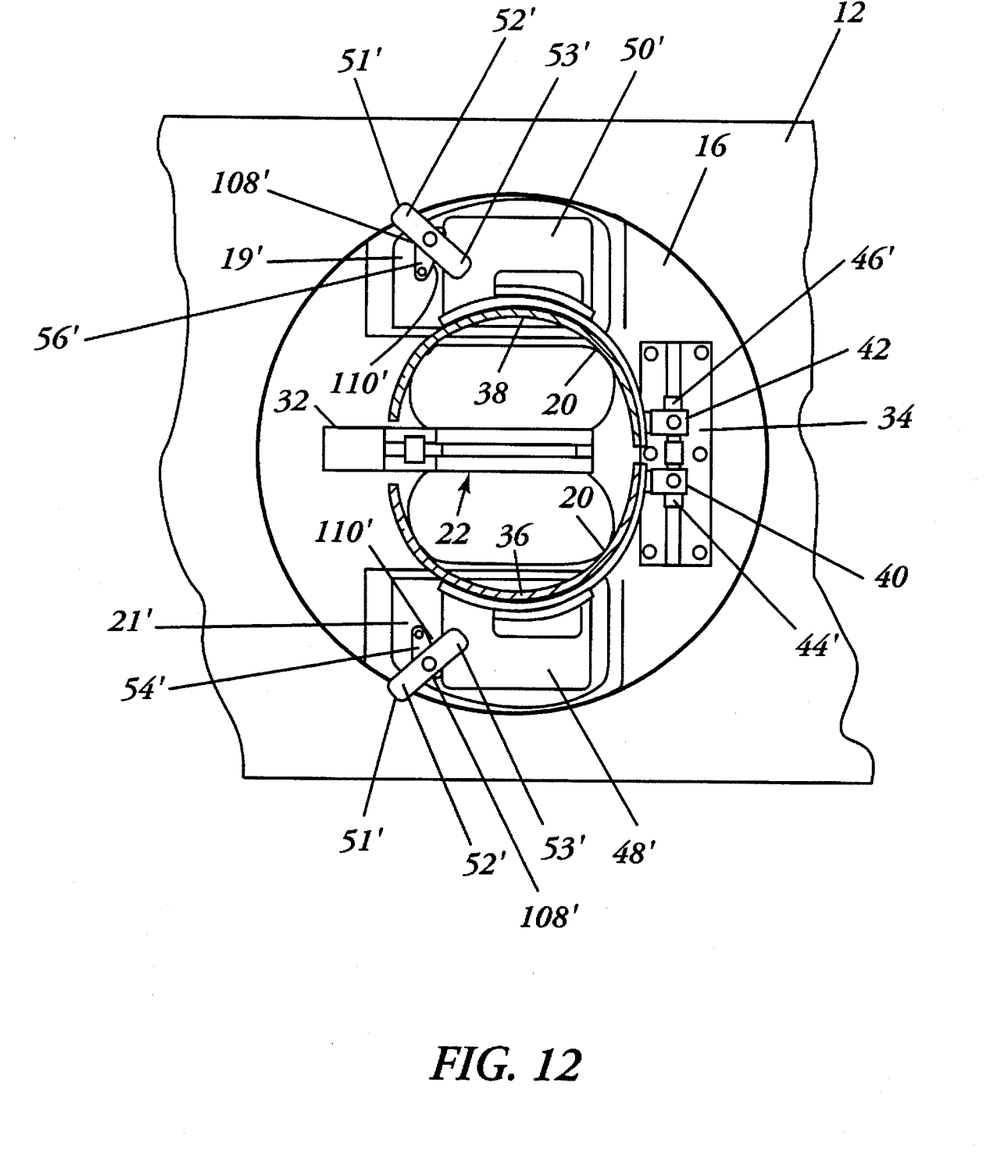
FIG. 12 is a view taken along line 12—12 of FIG. 11 including the improvements of the present invention and showing the side members in closed position.
Figure 13:
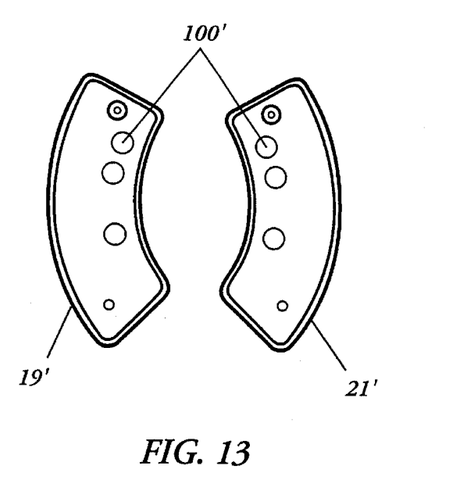
FIG. 13 is a top view of the glide strips of the present invention including the resilient pads.
Figure 14:
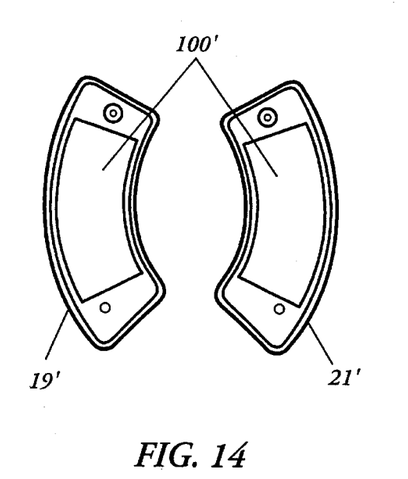
FIG. 14 is a top view of the glide strips of this invention including an alternative embodiment of the resilient pads.
Figure 15:
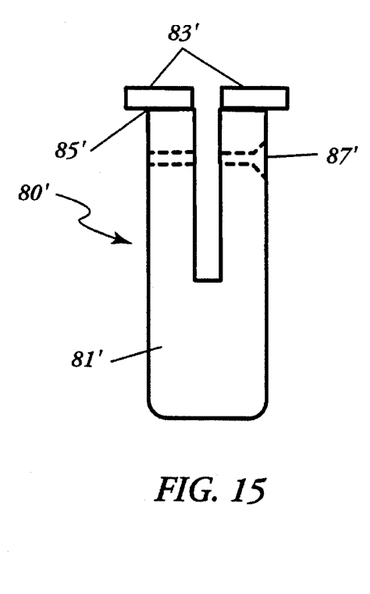
FIG. 15 is a top view of the improved latch of the present invention for securing the X-ray film cassette in a vertical position.
Figure 16:
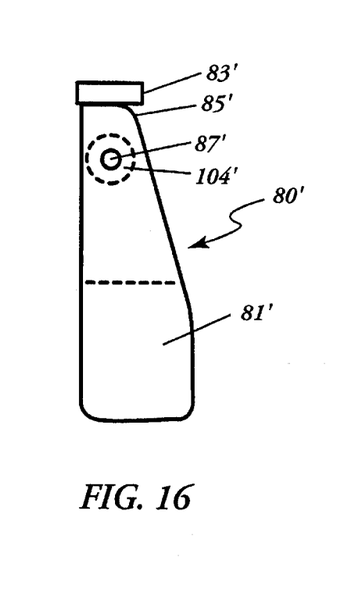
FIG. 16 is a side view of the improved latch of the present invention for securing the X-ray film cassette in a vertical position.
Figure 17:
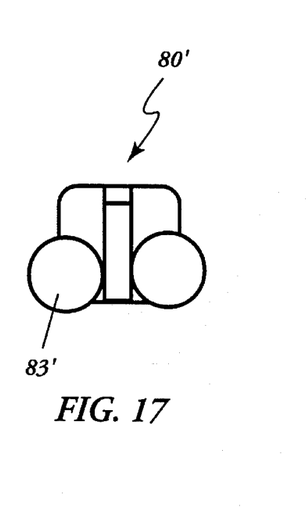
FIG. 17 is an end view of the improved latch of the present invention for securing the X-ray film cassette in a vertical position.

Referring now to FIGS. 12–14, the problem of securing the foot members 48' and 50' to the turn table 16 has been corrected by the addition of resilient pads 100' to the surface of glide strips 19' and 21'. Glide strips 19' and 21' are mounted between the turn table 16 and foot members 48' and 50'. The resilient pads 100' increase the friction between the glide strips 19' and 21' and the foot members 48' and 50' when buttons 52' are moved into place over foot members 48' and 50'. As depicted in FIG. 13, resilient pads 100' can be a number of small circular urethane disks, or as depicted in FIG. 14, can be broad flat pads that are substantially the same shape as glide strips 19' and 21'.

Referring now to FIGS. 11 and 15–17, the improvement in latch 80', which is used to secure carriage 78 at any position after carriage 78 is adjusted upward or downward, is the addition of resilient pads 83' to the end 85' of latch 80' that makes contact with carriage 78. Additionally, the end 81' of latch 80' opposite the end 85' having the resilient pad 83' is heavier than the end 85' having the resilient pad 83'. Latch 80' has a bore 87' for accepting a screw, a bolt or other means for attaching latch 80' to film holder 62'. This heavier end 81' obviates the need for extreme tightening at the pivot point 104' of latch 80' to film holder 62'. This prevents breakage in film holder 62'.

Figure 18:
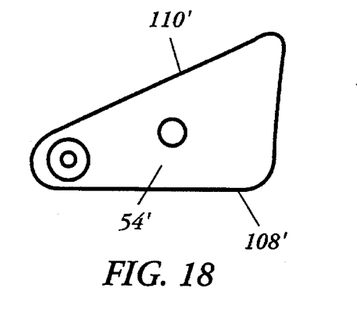
FIG. 18 is a front view of the block that supports the button that holds the foot members of this invention against the turn table.
Figures 19, 20:
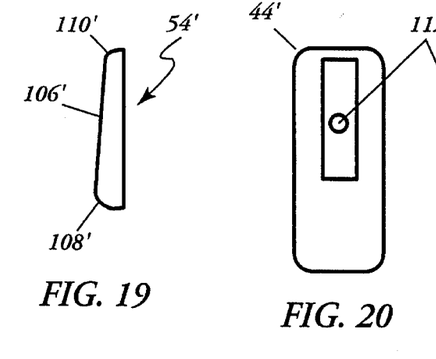
FIG. 19 is a side view of the improved block of the present invention that supports the button that holds the foot members of this invention against the turn table.
FIG. 20 is a front view of the improved sliding element of the present invention.

Blocks 54' and 56' that support buttons 52' have been recast for the positioner of this invention. Block 54' is described in detail in FIGS. 18–19. Block 56' is essentially identical to block 54', except that block 56' is designed for use on the opposite side of the positioner from block 54'. As best seen in FIGS. 18–19, block 54' is shaped substantially like a right triangle. The top surface 106' of block 54' is tapered as it proceeds from horizontal edge 108' towards hypotenuse edge 110'. Thus, block 54' is thicker near horizontal edge 108'.

Figure 10:
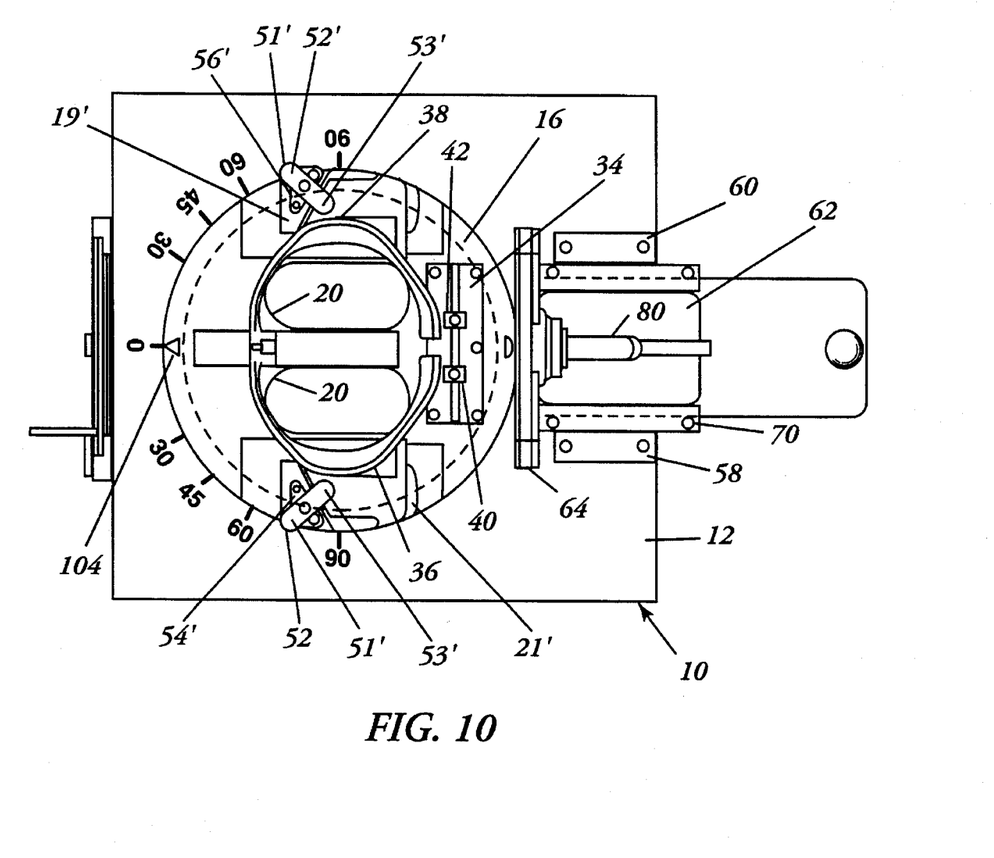
FIG. 10 is a top plan view of the positioner including the improvements of the present invention.

As seen in FIGS. 10 and 12, blocks 54' and 56' are mounted to glide strips 19' and 21'. Button 52' includes a mounting end 51' and a wedging end 53'. Button 52' is turnably mounted to blocks 54' and 56' at mounting end 51'. When button 52' is turned, wedging end 53' lies over foot members 48' and 50'. As button 52' is turned, the mounting end 51' of button is pushed up by the thicker horizontal edge 108' of blocks 54' and 56'. Wedging end 83' of button 52' is then pressed down onto foot members 48' and 50'. The taper of the top surface 106' of blocks 54' and 56' thus compensates for variable thickness in foot members 48' and 50', providing for a more secure latching of foot members 48' and 50'.

Figure 21:
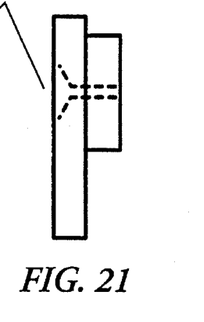
FIG. 21 is a side view of the improved sliding element of the present invention.

As best seen in FIGS. 12, 20 and 21, the sliding elements 44' and 46' used in the invention of this application are cast as a one-piece part. The previously described problems of separation of the two parts have thus been solved. Sliding elements 44' and 46' have a bore 112' for accepting a screw, a bolt or other means for attaching sliding elements 44' and 46' to upstanding side members 36 and 38. During the molding process, the thickness and dimension tolerance is held within a thousandth of an inch overall. This makes sliding elements 44' and 46' easily interchangeable with any of the positioner units that are presently on the market.

Figure 11:
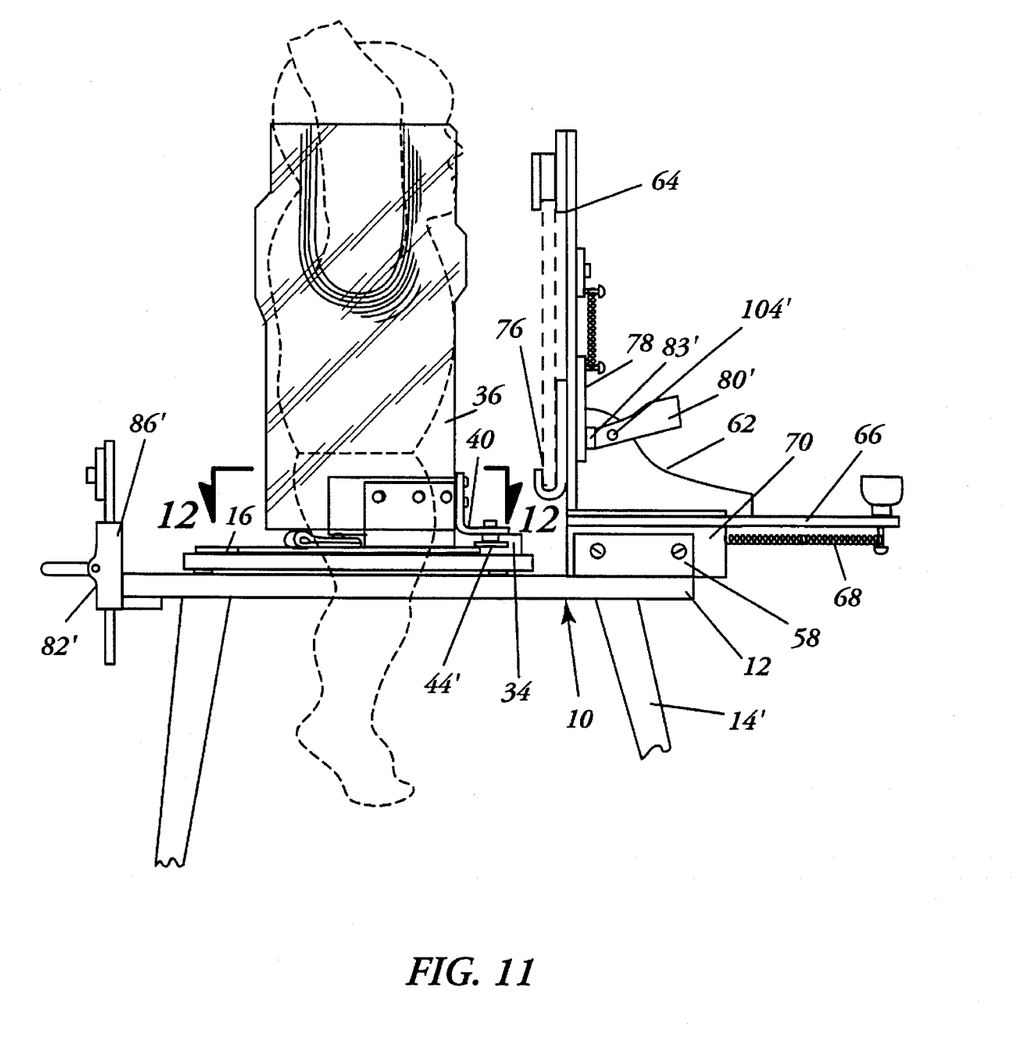
FIG. 11 is a side elevational view of the positioner including the improvements of this invention, the dotted line showing the body of a small child supported in the positioner.
Figure 22:
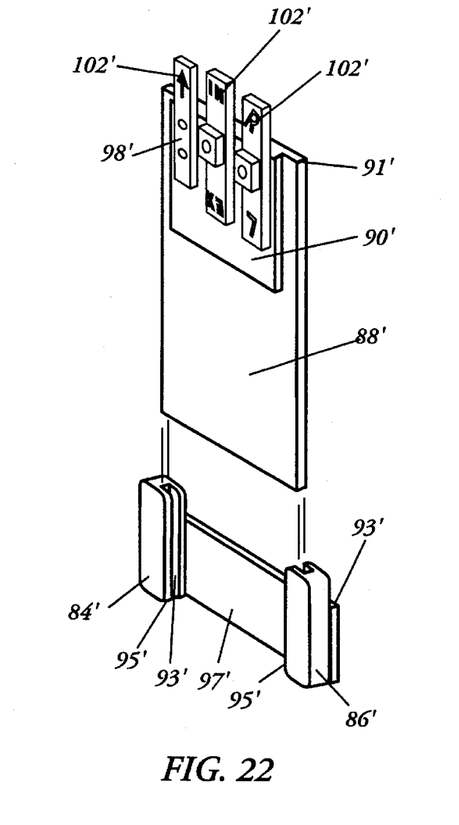
FIG. 22 is a perspective view of the improved device for displaying indicia of the present invention.

The device 82' for exposing identifying indicia to X-ray film has been modified. As seen in FIG. 11, device 82' is mounted on platform 12 between an X-ray source (not shown), and the upstanding members 36 and 38. As seen in FIG. 22, device 82' comprises a pair of vertically disposed slide blocks 84' and 86' that have a groove 93' in their faces 95' that face each other and that are connected by horizontal connecting member 97'. A board 88' is slidably mounted in the groove 93', and horizontal connecting member 97' lies adjacent to the bottom end 101' of board 88'. Board 88' carries plate 90' that is made of an X-ray impervious material such as lead. Indicia marker units 120' are mounted near the top end 91' of the plate 90' so that indicia 102' are positioned in the path of the X-ray. Indicia 102' includes figures that can communicate whether the X-ray was taken from the left or the right of the patient, whether the X-ray was taken when the patient was inhaling or exhaling, and which end of the X-ray film is the "up" end by displaying an arrow that points "up".

Figure 23:
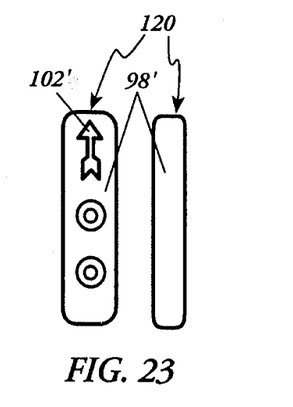
FIG. 23 is a front and side view of one of the indicia marker units of the present invention.
Figure 24:
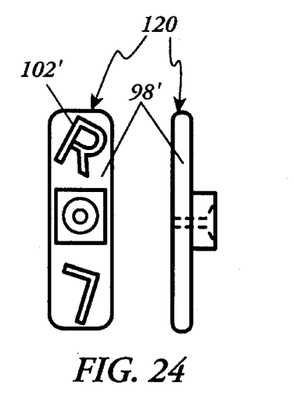
FIG. 24 is a front and side view of another indicia marker unit of the present invention.
Figure 25:
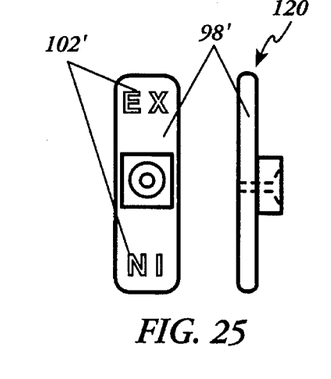
FIG. 25 is a front and side view of another indicia marker unit of the present invention.
Figure 26:
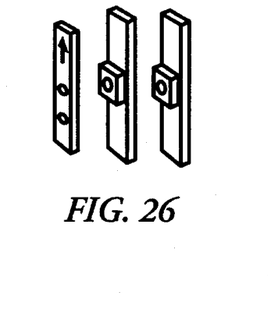
FIG. 26 is a perspective view of the three of the indicia maker unit of the present invention.
Figure 27:
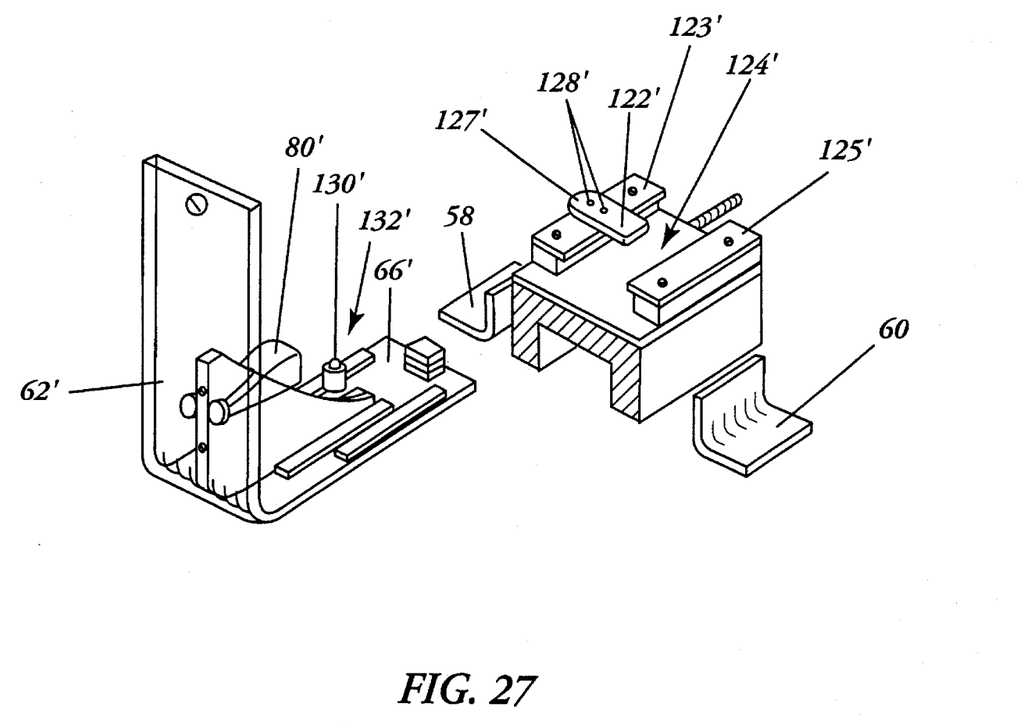
FIG. 27 is an exploded perspective view of the film holder and film holder track of the present invention.

The improvement, as seen in FIGS. 23–25, is that the indicia 102', which are made of an X-ray impervious material such as lead, have been cast in a mold with bar 98' so that the bar 98' and indicia 102' are one integral part, indicia marker unit 120'. The material from which the indicia marker unit 120' is molded is substantially unbreakable. An example of such a material is a urethane elastomer. Other examples would be apparent to one having ordinary skill in the art.

Indicia 102', which are preferably lead, are placed into a mold such that half the thickness of the indicia 102' protrudes into the cavity of the mold that is used to make bar 98'. A urethane elastomer is injected into the mold. When the elastomer hardened, indicia 102' is securely formed within bar 98'.

Another improvement provided in the invention of this application is an improved means for securing film holder 62' as it is moved towards and away from upstanding side members 36 and 38 that secure the child. As seen in FIGS. 27 and 33–35, film holder 62' fits into track 124' and can be moved towards and away from upstanding side members 36 and 38 in track 124'. Track 124' is formed by track defining blocks 123' and 125'. The improved means for securing film holder 62' comprise a latch 122' that is now mounted to track defining block 123' using means for mounting such as screws 128' that proceed from the top surface 127' of the latch 122' through latch 122' and into the track defining block 124'. Bores 135' are provided for screws 128'. A spring loaded pin 130' is mounted in a pin seat 132' on slide 66' of film holder 62'. Pin 130' fits into slot 131' in the bottom surface 133' of latch 122' as the film holder 62' is moved toward upstanding side members 36 and 38, thus securing film holder 62'

The seat latch 148' has been modified in this invention. The seat latch of this invention comprises parts that are molded under conditions wherein the tolerance is held within a thousandth of an inch. These parts include button 156' and seat latch base 158'. The resulting parts are interchangeable with any and all replacement parts of positioners that are on the market. Additionally, the latch 148' no longer includes pin 31.

Referring to FIGS. 28–32, seat latch comprises rod 150', bar 152', spring 154', button 156' and seat latch base 158'. Seat latch base 158' includes a substantially U-shaped section 162' formed within lower surface 161' of seat latch base 158' that faces turntable 16. U-shaped section 162' comprises a horizontal section 163' that is spaced away from turntable 16 and three vertical sections 164a', 164b', 164c' between horizontal section 163' and turntable 16. Vertical sections 164a' and 164c' are substantially parallel to one another and vertical section 164b' connects vertical section 164a' and 164c' and is substantially perpendicular to vertical sections 164a' and 164c'. Horizontal section 163' and vertical sections 164a', 164b', 164c' define space 167'.

Figures 28, 29, 30, 31:
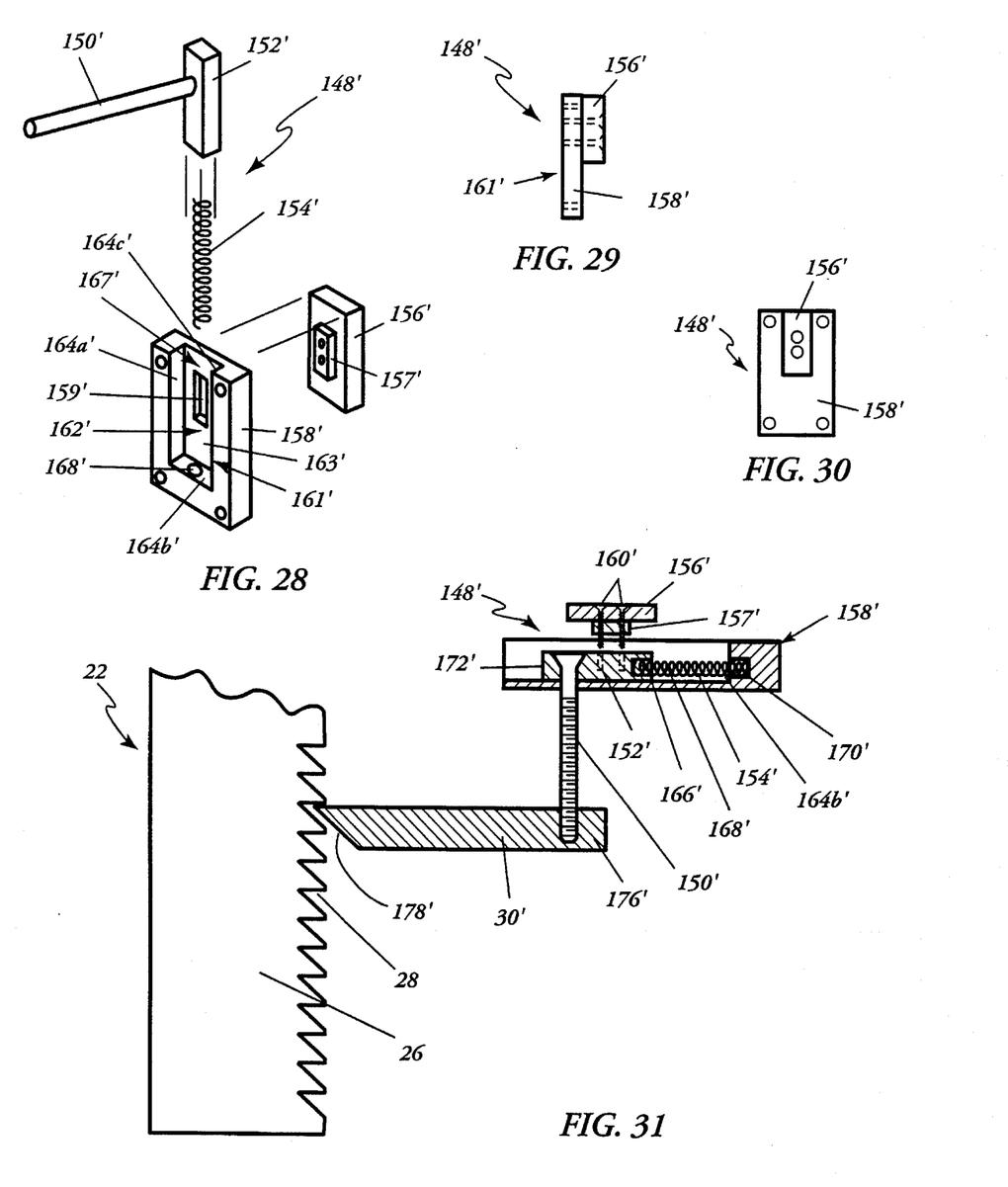
FIG. 28 is an exploded perspective view of the improved seat latch of the present invention.
FIG. 29 is a side view of the improved seat latch of the present invention.
FIG. 30 is a front view of the improved seat latch of the present invention.
FIG. 31 is an exploded side view of the seat latch of the present invention.

As best seen in FIGS. 28 and 31, platform 157' of button 156' is mounted within seat latch base 158' in medial slot 159' and button 156' mounted to bar 152' using screws 160' or the like. Bar 152' is slidably mounted within space 167' of seat latch base 158'. Spring 154' is also located in space 167' and is wedged between bar 152' and vertical section 164, of U-shaped seat latch base section 162' of seat latch base 158'. Spring 154' fits into bore 168' at the end 166' of bar 152' and into bore 170' in interior wall section 164'.

Figure 32:
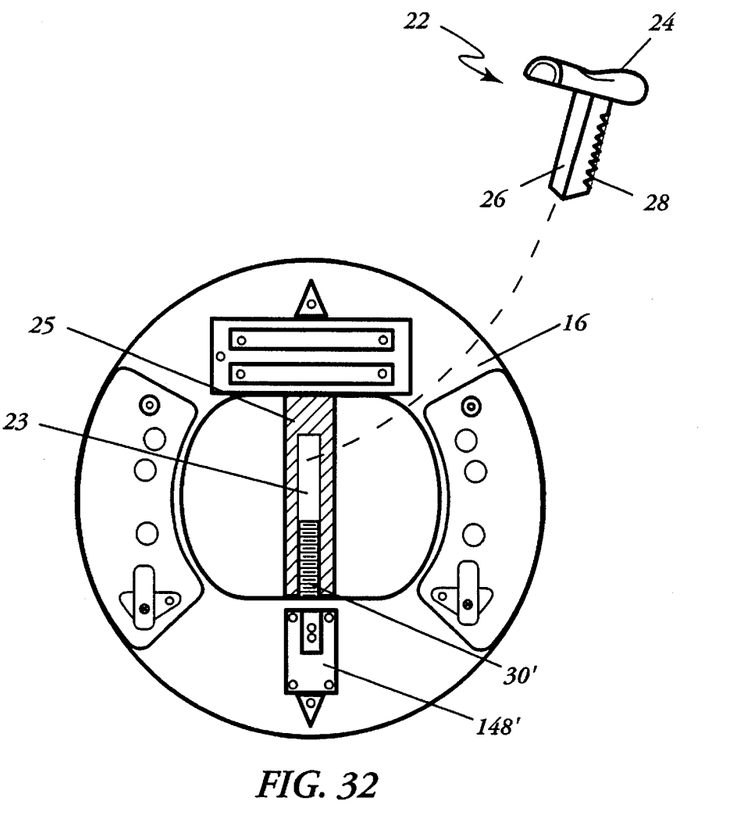
FIG. 32 is an exploded top view of the horse member and seat latch of the present invention, showing the interaction of the horse member and seat latch.
Figure 33:
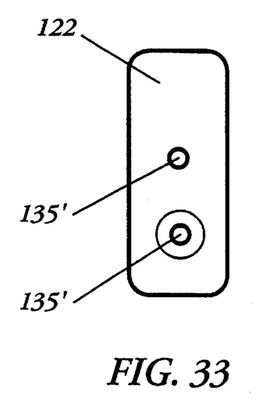
FIG. 33 is a top view of the improved latching means that is used in the improved means for securing the film holder as the film holder is moved laterally.
Figure 34:
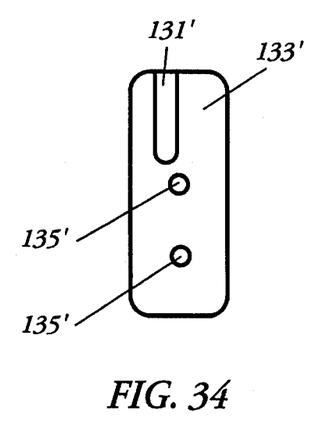
FIG. 34 is a bottom view of the improved latching means that is used in the improved means for securing the film holder as the film holder is moved laterally.
Figure 35:
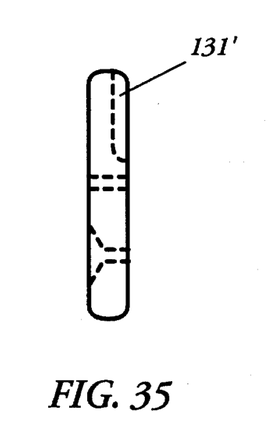
FIG. 35 is a side view of the improved latching means that is used in the improved means for securing the film holder as the film holder is moved laterally.

Continuing on FIGS. 31–32, rod 150' is mounted in the end 172' of bar 152' that is opposite end 166' where spring 154' is mounted. Rod 150' extends downward from bar 152' and into end 176' of dog 30'. The other end 178' of dog 30' fits into pawl teeth 28 of bar 26 of horse member 22.

Referring to FIG. 32, horse member 22 fits into slot 23 of board 25 that is mounted beneath turntable 16. Dog 30' fits into pawl teeth 28 of bar 26 of horse member 22. Seat latch 148' works as follows. Referring to FIGS. 31–32, the user moves button 152' away from horse member 22 and towards the periphery of turntable 16. Button 152' moves bar 152' towards interior wall section 164' of seat latch base 158'. Spring 154' is compressed. As bar 152' moves, rod 150' moves and removes dog 30' from pawl teeth 28. Horse member 22 is released and can be adjusted to the desired height. After horse member 22 is adjusted, button 152' is released. Spring 154' expands, propelling bar 152' away from interior wall section 164'. Bar 152' moves rod 150' moves and replaces dog 30' into pawl teeth 28. Horse member 22 is thus secured in place. Spring 154' does not bind within latch 148', and smooth and effective latching results.

Thus, although there have been described particular embodiments of the present invention of a new and useful improvements in a positioner for a child being X-rayed, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. An improvement in a positioner for a child being X-rayed, the positioner comprising a platform having an opening therethrough, a turn table mounted in the opening in said platform for rotary movement in clockwise and counterclockwise directions, there being a pair of side-by-side spaced openings in said turn table between the perimeter thereof for the projection of the legs of a child therethrough, a horse member arranged between and spaced from each of said openings for supporting a child in a straddled position and connected to said turn table for upward and downward movement, a pair of arcuate shaped upstanding side members each transparent to light waves and X-rays arranged in face-to-face spaced relation positioned on said turn table between the perimeter and said turn table openings and connected to said turn table for limited movement toward and away from each other, and an upstanding film holder positioned on said platform adjacent to and facing said side members and supported on said platform, the film holder including latching means for latching an X-ray film cassette in place after movement of the X-ray film cassette vertically to place the X-ray film cassette between an X-ray machine and the child being X-rayed, the latching means having an end that contacts the X-ray film cassette and an end opposite the end that contacts the X-ray film cassette, the improvement comprising means for increasing fiction mounted at the end of the latching means that contacts the X-ray film cassette and the end of the latching means opposite the end that contacts the X-ray film cassette having a greater weight than the end that contacts the X-ray film cassette.

2. An improvement in the positioner for a child being X-rayed described in claim 1, the positioner further comprising foot members attached to said arcuate shaped upstanding side members, glide strips mounted between said foot members and said turn table, and latching means for latching said foot members to said glide strips mounted on said glide strips, the improvement comprising means for increasing friction mounted between said glide strips and said foot members.

3. An improvement in the positioner for a child being X-rayed described in claim 1, the positioner further comprising means for displaying indicia mounted on the platform such that said means for displaying indicia fail in a path of an X-ray from an X-ray machine and the X-ray film cassette, the means for displaying indicia including indicia and indicia supporting means for supporting indicia, the improvement comprising said indicia being molded into said indicia supporting means so that said indicia are an integral unit with said indicia supporting means.

4. An improvement in the positioner for a child being X-rayed described in claim 1, the positioner further comprising a track into which the film holder is mounted, the film holder including a slide that fits into said track, the improvement comprising securing means for securing the film holder when the film holder is moved towards or away from said pair of arcuate shaped upstanding members, said securing means comprising a latching means mounted on said track and stop means comprising a spring loaded pin mounted on said slide of said film holder such that said pin interacts with said latching means.

5. An improvement in the positioner for a child being X-rayed described in claim 2, the positioner further comprising securing means for securing said foot members to said glide strips, said securing means having a mounting end and a wedging end, said securing means turnably mounted to said glide strips, the improvement comprising tightening means for tightening said securing means against said foot members.

6. An improvement in the positioner for a child being X-rayed described in claim 5, wherein the positioner further comprises said securing means mounted at its said mounting end on a support means for supporting said securing means, said support means mounted to said glide strip; and wherein said tightening means comprises said support means being tapered along a top surface of said support means, said top surface lying adjacent to said securing means, such that said support means is thicker at a point where said mounting end of said securing means contacts said top surface when said wedging end of said securing means is moved over said foot members.

7. An improvement in a positioner for a child being X-rayed as described in claim 1, the positioner further comprising a latching means for latching said horse member to said turntable, said horse member further comprising a seat member and a bar extending downward from said seat member, the bar having a plurality of receiving means for receiving said latching means along a vertical edge of said bar; the latching means comprising a base mounted to said turntable, said base having a medial slot therein and a lower surface facing said turntable, said surface having a horizontal section spaced away from said turntable and three vertical sections between said horizontal section and said turntable, two of said vertical sections being substantially parallel to one another and the third of said vertical sections connecting said parallel vertical sections and being substantially perpendicular thereto, said horizontal section and said vertical sections defining a space between said turntable and said base; a bar slidably mounted within said space, a button mounted within said base at said medial slot, said button mounted to said bar; a rod extending downward from said bar; a dog having two ends, said dog attached at one of its ends to said rod, said dog having at is other end interacting means for interacting with said receiving means of said bar of said horse member to latch said horse member in place;

the improvement comprising a spring mounted within said space between said bar and said connecting vertical section of said lower surface of said base.

8. An improvement in the positioner for a child being X-rayed described in claim 7, wherein the improvement further comprises said base being cast as a one-piece part.

9. An improvement in the positioner for a child being X-rayed described in claim 1, wherein the positioner further comprises sliding elements mounted to a base of said arcuate shaped upstanding members, said sliding elements slidably mounted to said turntable, the improvement comprising said sliding elements being cast as a one-piece part.

* * * * *